(12) United States Patent
Fatiny

(10) Patent No.: US 8,435,035 B1
(45) Date of Patent: May 7, 2013

(54) DENTAL INSTRUMENT

(75) Inventor: Fahad Ibrahim Fatiny, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/298,160

(22) Filed: Nov. 16, 2011

(51) Int. Cl.
*A61C 3/00* (2006.01)

(52) U.S. Cl.
USPC ........................................ 433/149

(58) Field of Classification Search ......... 433/114, 433/141, 143, 144, 145, 149, 25, 34, 37, 433/40, 125, 164, 142, 148, 215, 216; 606/53, 606/79, 84; D24/146, 152, 154, 156, 176; 600/210, 237
See application file for complete search history.

(56) References Cited

U.S. PATENT DOCUMENTS

| | | | |
|---|---|---|---|
| 739,333 A | 9/1903 | Miles, Jr. | |
| 1,109,924 A | 9/1914 | Hoffman et al. | |
| 2,056,417 A | 10/1936 | Bosworth | |
| 2,674,799 A | 4/1954 | Fraser | |
| 4,270,902 A * | 6/1981 | Wiland | 433/144 |
| 4,315,745 A | 2/1982 | Murata | |
| 4,365,957 A * | 12/1982 | Das | 433/144 |
| 4,854,867 A * | 8/1989 | Meinershagen | 433/40 |
| 5,830,225 A | 11/1998 | Detsch | |
| 5,934,905 A * | 8/1999 | Martoral et al. | 433/144 |
| 6,309,219 B1 | 10/2001 | Robert | |
| 2005/0095558 A1 * | 5/2005 | Jones | 433/144 |
| 2006/0063130 A1 * | 3/2006 | Hayman et al. | 433/141 |
| 2006/0160046 A1 * | 7/2006 | Nesbitt et al. | 433/88 |
| 2009/0042165 A1 | 2/2009 | Garrison et al. | |

FOREIGN PATENT DOCUMENTS

| | | |
|---|---|---|
| EP | 2260787 | 12/2010 |
| WO | WO 2005/079693 | 9/2005 |
| WO | WO 2009/118741 | 10/2009 |

OTHER PUBLICATIONS

Website, http://www.kabdental.com/small-dental-equipment/miltex_instruments_and_products/elevators.htm, series of dental instruments, 11 pages printed from the internet on Jun. 13, 2011.

* cited by examiner

*Primary Examiner* — Cris L Rodriguez
*Assistant Examiner* — Justin O'Donnell
(74) *Attorney, Agent, or Firm* — Richard C. Litman

(57) ABSTRACT

The dental instrument is formed of a single elongate, unitary length of surgical steel or other suitable material. The instrument preferably includes two mutually opposed working end portions and a generally medial cushioned handgrip portion. Each of the end portions has a shallow axial channel and a sharpened distal end having a notch formed therein. The two sides of the notch provide two contact points or areas to avoid the extreme pressures applied by conventional single contact point instruments and the resulting breakage of the tooth and subsequent difficulty in extracting the base or root of the tooth that often occurs. A lateral notch having sharpened edges is also preferably formed along one side of each working end portion of the tool. The configuration of the dental instrument provides greater versatility to perform the manipulations generally required for tooth extraction.

5 Claims, 3 Drawing Sheets

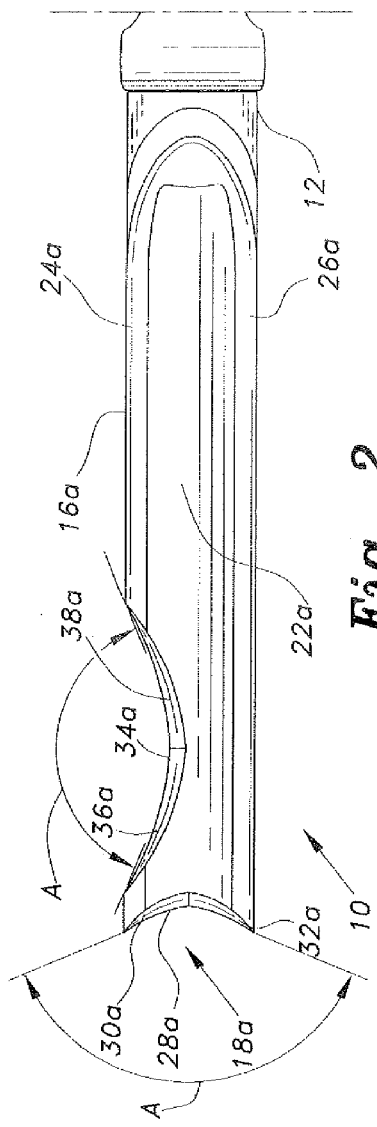
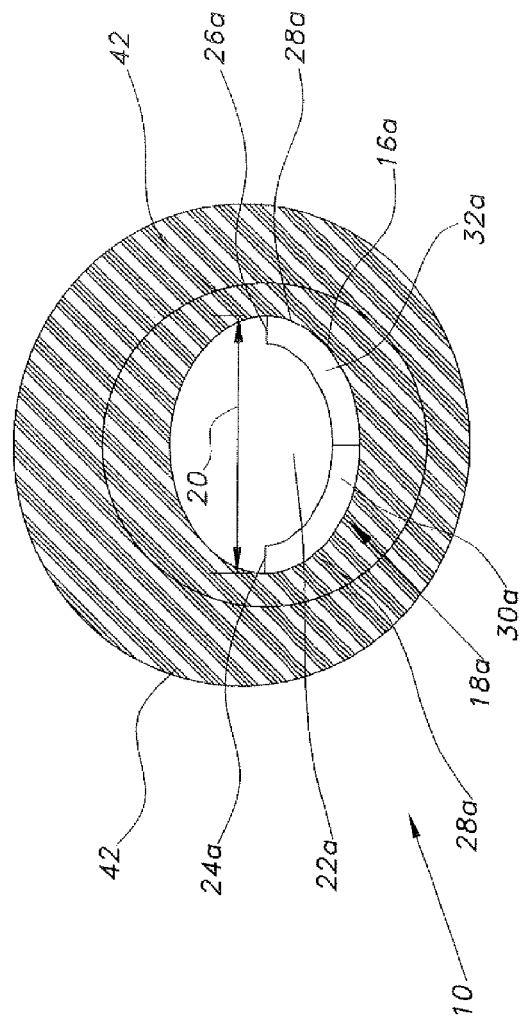

DENTAL INSTRUMENT

BACKGROUND OF THE INVENTION

1. Field of the Invention

The present invention relates to tools, instruments, and implements used in the medical field, and particularly to a manual dental instrument for elevating and luxating or loosening teeth in preparation for extraction.

2. Description of the Related Art

Although modern medical science and technology have greatly improved the ability of dentists and other medical professionals to retain the natural teeth for their patients, from time to time it is still necessary to extract a natural tooth. Such tooth extractions must still be accomplished by hand, using manual tools for the most part. Accordingly, a number of different tools and instruments have been developed in the past, for extracting a tooth or preparing a tooth for extraction.

Most of these instruments used for the preparation of extraction, i.e., luxating or loosening the tooth, are shaped or contoured to provide only a single contact point, or at most a single short line of contact, between the tooth and the instrument. The resulting very high localized pressure can often result in the tooth breaking before the root has been loosened sufficiently to facilitate extraction. When this occurs, the dentist or dental professional is left with a considerably more complex and time-consuming operation to remove the remaining tooth. This additional work results in additional trauma for the patient.

None of the above inventions and patents, taken either singly or in combination, is seen to describe the instant invention as claimed. Thus, a dental instrument solving the aforementioned problems is desired.

SUMMARY OF THE INVENTION

The dental instrument is formed of a single elongate, unitary length of surgical steel or other suitable material. The instrument preferably includes two mutually opposed working end portions and a generally medial cushioned handgrip portion. Each of the end portions has a shallow axial channel with a sharpened distal end having a notch formed therein. The two sides of the notch provide two contact points or areas to avoid the extreme pressures applied by conventional single contact point instruments and the resulting breakage of the tooth and subsequent difficulty in extracting the base or root of the tooth that often occurs. A lateral notch having sharpened edges is also preferably formed along one side of each working end portion of the tool.

The configuration of the dental instrument provides greater versatility to perform the manipulations generally required for tooth extraction. The instrument enables the dental professional to luxate or loosen the subject tooth prior to extraction by prying or levering the tooth angularly, and provides some ability to rotate the tooth axially as well in order to luxate the tooth prior to applying forceps for the actual extraction. The sharpened blades of the distal end notch of the dental instrument also enable the dental professional to cut the tissue surrounding the subject tooth, thereby further facilitating the removal of the tooth.

These and other features of the present invention will become readily apparent upon further review of the following specification and drawings.

BRIEF DESCRIPTION OF THE DRAWINGS

FIG. 2 is a partial detailed top plan view of one of the working end portions of the dental instrument according to the present invention, illustrating further details thereof.

FIG. 3 is an end elevation view of the dental instrument according to the present invention, illustrating further details thereof.

Similar reference characters denote corresponding features consistently throughout the attached drawings.

DETAILED DESCRIPTION OF THE PREFERRED EMBODIMENTS

Figure 1:
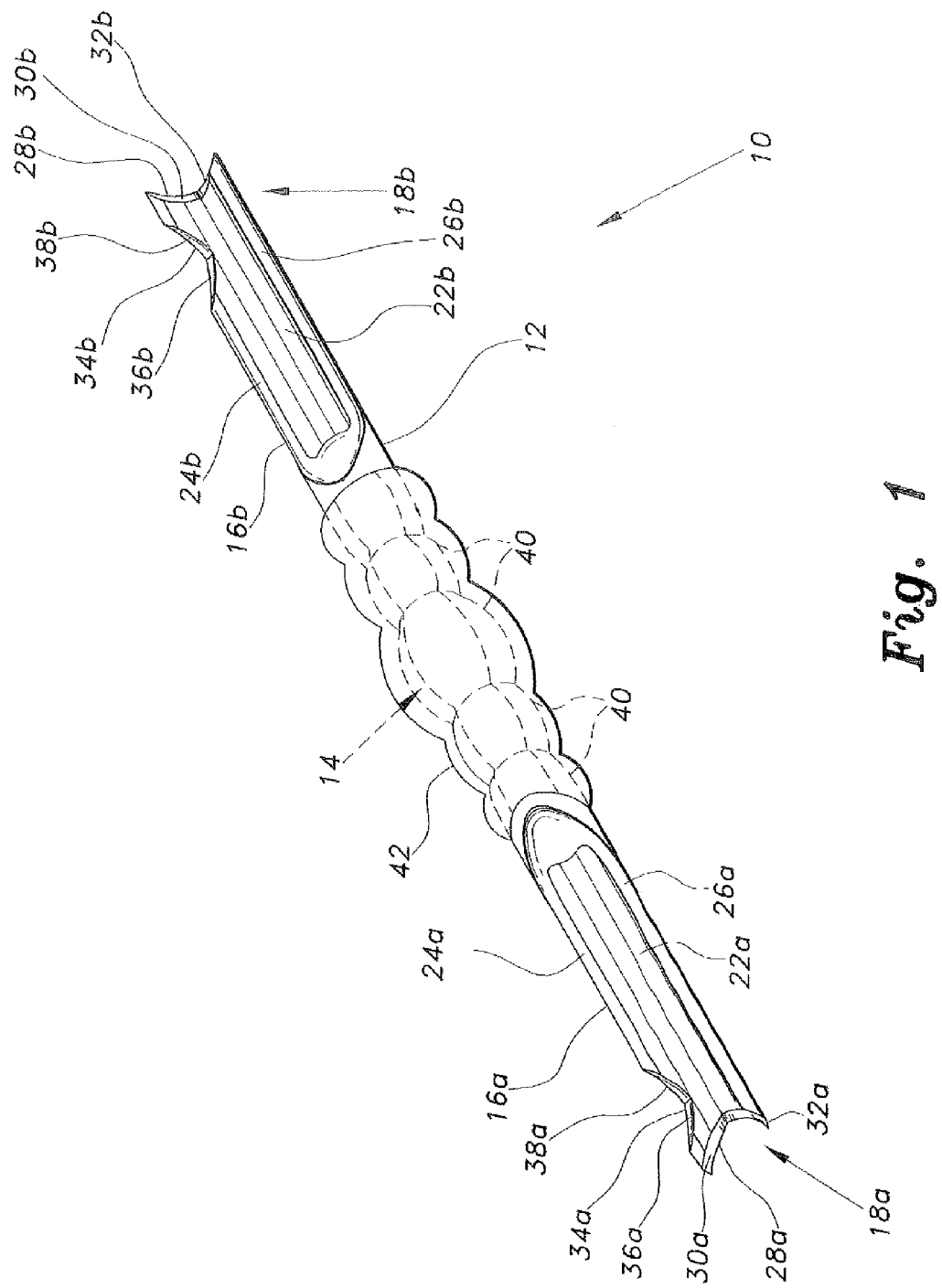
FIG. 1 is a perspective view of a dental instrument according to the present invention, illustrating its general configuration and features.
Figure 4:
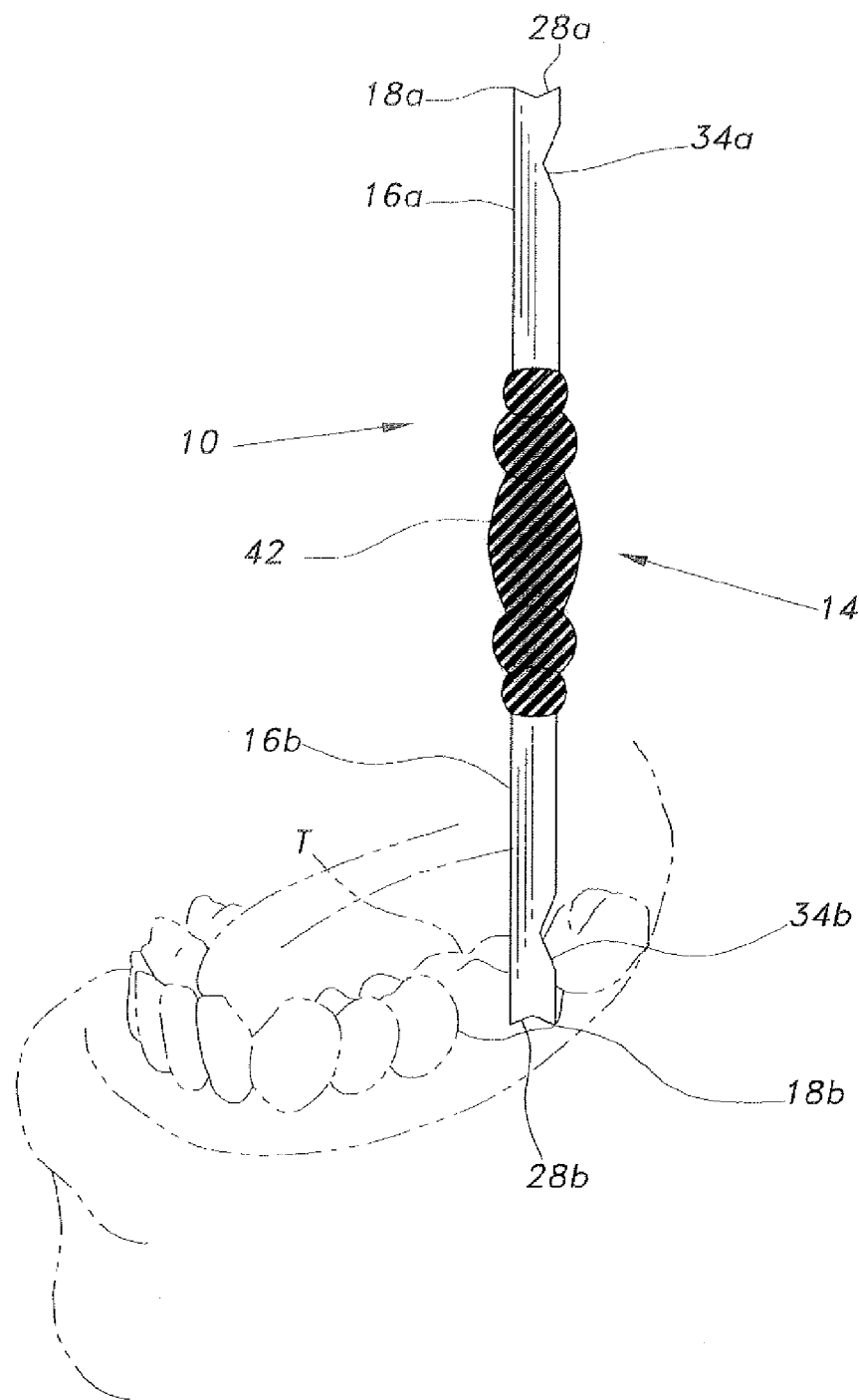
FIG. 4 is an environmental perspective view of the dental instrument according to the present invention, illustrating an exemplary manipulation of the instrument in preparation for the extraction of a tooth.

The dental instrument enables the dental professional to luxate or loosen a tooth prior to extraction. FIGS. 1 and 4 provide an enlarged perspective view of the dental instrument 10, illustrating its general features. The dental instrument 10 is formed of a rigid, continuous, straight elongate rod 12 of surgical steel or other suitable material, and has a generally medial handle portion 14 and at least one working portion. The embodiment of the instrument 10 shown in FIGS. 1 and 4 includes two mutually opposed working portions 16*a* and 16*b*, which are mirror images of one another. Each of the working portions 16*a* and 16*b* includes a distal tip 18*a* and 18*b* opposite the central handle portion 14.

FIG. 3 of the drawings provides an end elevation view of the first working end 18*a* of the dental instrument 10. This end elevation view shows that the rod or shank of the tool 10 has a generally elliptical cross section, having a major diameter 20. Each working portion of the rod 12 is formed with a shallow channel therein that extends from adjacent the handle portion 14 to the tip of the respective working portion, e.g., the channel 22*a* of the working portion 16*a* of the tool 10 as shown in FIG. 3, with the opposite working portion 16*b* having a corresponding shallow channel 22*b*, as shown in FIG. 1. The channel 22*a* is defined by its mutually opposed, coplanar and parallel channel edges 24*a* and 26*a*, and the opposite channel 24*a* has a similar configuration defined by its channel edges 24*b* and 26*b*. Each of the channel edges comprises a flat surface. The planes forming the two flat surfaces of each channel edge pair, e.g., channel edges 24*a* and 26*a*, are coplanar with one another.

The tip 18*a*, 18*b* of each working portion 16*a*, 16*b* is formed with a notched and sharpened edge, respectively 28*a* and 28*b*. The notches preferably define an included angle A of about 135°, as shown most clearly in the top plan view of the working portion 16*a* of the instrument 10 in FIG. 2. Other notch angles may be provided. The notched tips 18*a*, 18*b* of the instrument 10 are beveled. The beveled surfaces 30*a*, 32*a* and 30*b*, 32*b* result in the sharpened cutting edges 28*a* and 28*b* for the notched tips 18*a* and 18*b*. In addition, one of the channel edges of each working portion 16*a* and 16*b* may include a notch therein, as shown by channel edge notch 34*a* of the first channel edge 24*a* of the first working portion 16*a* and channel edge notch 34*b* of the first channel edge 24*b* of the second working portion 16*b*. The configurations of the two channel edge notches 34*a* and 34*b* are similar to the two notched tips 18*a* and 18*b* of the two working portions 16*a*, 16*b* of the tool 10. The first working portion channel edge notch 34*a* has first and second beveled surfaces 36*a* and 38*a*, and the second working portion channel edge notch 34*b* has first and second beveled surfaces 36*b* and 38*b* to form their respective sharpened edges. The included angle A of the two channel edge notches 34*a* and 34*b* is preferably about 135°, as shown for the channel edge notch 34a in the plan view of FIG. 2. The channel edge sharpened notches 34a and 34b provide additional flexibility in the use of the dental instrument 10 in prying or otherwise luxating a tooth in preparation for its extraction.

The dental instrument 10 is formed with a series of convex and mutually adjacent knobs 40 disposed axially therealong and surrounding the medial handle portion 14 of the instrument 10. The knobs 40 preferably increase in diameter from the first knob adjacent the respective working end 16a and 16b of the instrument 10 to a medial largest diameter knob. Each of the knobs 40 has a circular cross section that is somewhat larger than the major diameter 20 of the elliptical cross section of the working portion of the instrument 10, as shown in the end view of FIG. 3. A resilient handgrip 42 is molded or otherwise formed over the knobs 40 of the medial portion 14 of the instrument 10. The handgrip 42 material preferably comprises a pliable material having a high surface coefficient of friction, e.g., Neoprene® or other suitable material having similar properties. The resilient material of the handgrip 42 is preferably molded or otherwise formed to conform to the different diameters of the underlying knobs 40 in order to provide a good grip for the dentist or dental professional using the instrument 10.

FIG. 4 of the drawings provides an illustration of the dental instrument 10 as it might be used for luxating a tooth T in preparation for extraction of the tooth. The tip 18b of the first working end 16b may be worked alongside the subject tooth T, or perhaps levered between adjacent teeth as a result of the relatively thin material defining the channel 22a. The opposite working end 16a may be used in a similar manner, as desired. The instrument 10 may be worked around the tooth T to loosen the tooth within its socket. The two beveled surfaces 30a and 32a (shown in FIGS. 1 through 3) result in two contact points or lines across the beveled surfaces to greatly reduce point pressure on the tooth. This greatly reduces the chances of the tooth T fracturing across its diameter, and the subsequent need to remove the base of the tooth from the socket and the accompanying difficulties and additional trauma that such a procedure entails for the patient. Accordingly, the dental instrument 10 will serve to facilitate and ease the procedure of luxating a tooth in preparation for its extraction during dental procedures.

It is to be understood that the present invention is not limited to the embodiments described above, but encompasses any and all embodiments within the scope of the following claims.

I claim:

1. A dental instrument for luxating and axially rotating a tooth, comprising a rigid, elongate, rod having:
    a handle portion, the handle portion having opposing ends;
    mutually opposed first and second working portions in mirror image to one another and located on respective opposing ends of the handle portion, each of the working portions including a distal tip opposite the handle portion and a generally elliptical cross section defining a major axis, the elliptical cross section further defining a shallow channel formed along the working portion and extending to the distal tip, the channel being defined by a first and second channel edge, wherein the first and second channel edges are mutually opposed, coplanar, and coincident with the major axis of the elliptical cross section; and
    the tip has a single notched and sharpened edge subtending an included obtuse angle extending between the first and second channel edges, wherein the first channel edge includes a sharpened notch therein and the second channel edge has a straight length extending from the handle portion to the distal tip, wherein the first and second channel edges of the channel comprise coplanar flat surfaces spaced rearwardly away from the distal tip.

2. The dental instrument according to claim 1, wherein said handle portion being disposed medially between the first and second working portions, the handle portion having a plurality of mutually adjacent knobs disposed axially therealong, each of the knobs having a circular cross section of larger diameter than the major axis of the working portions, each of the knobs surrounding the handle portion, the handle portion further comprising a resilient handgrip disposed over the handle portion, the resilient handgrip having an exterior configuration generally conforming to the configuration of the underlying handle portion.

3. The dental instrument according to claim 1 further comprising a resilient handgrip disposed over the handle portion.

4. The dental instrument according to claim 1, wherein the rod is formed of surgical steel.

5. The dental instrument according to claim 1 wherein the obtuse angle is about 135°.

* * * * *